United States Patent [19]
Fong et al.

[11] Patent Number: 4,640,932
[45] Date of Patent: Feb. 3, 1987

[54] COMPOSITIONS FOR TREATING ACNE VULGARIS AND METHODS OF MAKING AND USING SAME

[75] Inventors: John Fong; Mitchell S. Wortzman, both of Los Angeles; Richard A. Scott, Burbank, all of Calif.

[73] Assignee: Neutrogena Corporation, Los Angeles, Calif.

[21] Appl. No.: 713,211

[22] Filed: Mar. 18, 1985

[51] Int. Cl.$^4$ ........................................... A61K 31/075
[52] U.S. Cl. ................................... 514/714; 514/859; 514/949
[58] Field of Search ........................ 514/714, 859, 949

[56] References Cited

U.S. PATENT DOCUMENTS 4,056,611  11/1977  Young ................................. 514/714

OTHER PUBLICATIONS

Chemical Abstracts 90: 597h (Gloor et al.) 1979.

*Primary Examiner*—Leonard Schenkman
*Attorney, Agent, or Firm*—Richard R. Mybeck

[57] ABSTRACT

A composition comprising a unique facial mask containing benzoyl peroxide as its essential active ingredient which provides a surprisingly effective, efficient and acceptable method to control and mitigate acne vulgaris in individuals susceptible thereto.

5 Claims, No Drawings

4,640,932

COMPOSITIONS FOR TREATING ACNE VULGARIS AND METHODS OF MAKING AND USING SAME

TECHNICAL FIELD

The present invention relates to new and improved means for treating acne vulgaris; a unique facial mask containing benzoyl peroxide as its essential active ingredient which is surprisingly compatible therewith and effective to control and mitigate acne vulgaris in those individuals susceptible thereto; and a unique method for producing a chemically and physically stable mask composition which is efficacious in the treatment of acne vulgaris and cosmetically pleasing to use.

BACKGROUND ART

The cause of acne vulgaris is unknown but recent research has provided insight into the pathogenesis of the condition. Currently, there is general agreement that the relevant factors are an individual'genetic predisposition to acne, the size of an individual's sebaceous gland (See: Cunliffe et al, *The Acnes: Clincial Features, Pathogensis and Treatment.* W. B. Saunders Co., London, pp 62, 66–67, 1975), the type and quantity of bacteria within the follicle (See: Marples et al, "Control of Free Fatty Acid in Human Surface Lipids . . . " *Journal of Investigative Dermatology*, 56, 127–131, 1971; Mill et al, "Acne Vulgaris Oral Therapy With Tetracycline and Topical Therapy . . . ", *Archives of Dermatology*, 106, 200–203, 1972), the androgenic stimulation of sebum (See: Shalita , "Acne Vulgaris Current Concepts in Pathogenesis Treatment International", *Journal of Dermatology*, 15, 182–187, 1976), and alterations in the keratinization process (See: Holms et al, "Pilosebaceous Duct Obstruction in Acne", *British Journal of Dermatology*, 87, 327-33).

Benzoyl peroxide was first considered for the treatment of acne vulgaris in 1934 but was not fully appreciated until recently because of insufficient understanding of the role the vehicle plays in delivering the medication to the pilosebaceous apparatus.

The vehicles heretofore attempted included cremes, lotions and hydroalcohol gels containing from 2.5 to 20% benzoyl peroxide. Such formulations received wide acceptance mostly because of the ability of benzoyl peroxide to inhibit *P.acnes* in vivo.

Further, benzoyl peroxide was considered to be quite versatile since it achieved demonstrated success in treating all forms and grades of acne except acne conglobata, that is, grade 4 cystic acne. (See: Hurwitz et al, "How to Individualize Acne Therapy", *Patient Care.* 17, 133–167, 1983).

However these formulations were also found unable to avoid the keratolytic or desquamating effect of benzoyl peroxide as demonstrated by the irritation accompanying its use.

Furthermore such commerical products have the tendency to deliver benzoyl peroxide to systemic locations where it is not needed and in forms in which it is not active.

Thus a need exists for a product which can be used to effectively treat the common forms of acne and expecially acne vulgaris, while avoiding the untoward side effects and inconvenience inherent in the prior art formulations and providing a readily applied, easily used, cosmetically pleasant and commercially acceptable product.

SUMMARY OF INVENTION

The present invention presents compositions and methods of making and using same which commpositions are remarkably useful for treating acne. The present invention is predicted upon the production of an uniquely compatible facial mask capable of containing as its essential active ingredient from about 0.5 percent to about 10 percent by weight of benzoyl peroxide and which in use obtains a remarkably unexpected beneficial effect as shall hereinafter appear in greater detail.

Accordingly, it is a prime object of the present invention to provide new and improved means and methods for delivering benzoyl peroxide to acne sites which enhance the effectiveness of the active therapeutic agent while substantially reducing the treatment period associated with prior art products.

A further object of the present invention is to provide a new and improved product for the treatment of acne which not only achieves direct therapeutic action but achieves a secondary benefit by attracting excess sebum from the situs thereby substantially eliminating its influence on the further replication of the acne condition.

Still another object of the present invention is to provide improved means and methods for treating acne sites which treatment is of short duration and may be thereafter washed off permitting the user to engage in normal social activity.

Still a further object of the present invention is to provide new and useful compositions and articles of manufacture which contain benzoyl peroxide at levels effective to treat acne vulgaris.

A still further object of the present invention is to provide a novel and unique mask composition which is physically and chemically stable when admixed with benzoyl peroxide at designated levels and which is effective in the treatment of acne vulgaris without degradation of active components or deterioration of the mask system.

These and still further objects as shall hereinafter appear are readily fulfilled by the present invention in a remarkably unexpected manner as will be readily discerned from the following detailed description of an exemplary embodiment thereof.

MODES FOR CARRYING OUT THE INVENTION

The product of the present invention comprises a unique highly stable formulation in which from about 0.5 to about 10% by weight of benzoyl peroxide is strategically disposed throughout a specially formulated facial mask which is non-gritty and cosmetically pleasing to use.

The facial mask of the present invention comprises a mixture of inorganic thickening agents, absorbent powders, and/or organic gelling agents, with or without alcohol. In practice, suitable inorganic thickening agents include Veegum (magnesium aluminum silicate), and Bentonite. Suitable organic gelling agents include gelatin, starch, cellulosic gums, guar gum, alginates, and polyvinyl alcohols.

Other ingredients heretofore employed in the production of conventional facial masks may also be incorporated in the compositions of the present invention so long as they do not affect the ultimate stability of the composition. Typical among such compatible additives are propylene glycol, which serves as a humectant, and methyl and ethyl paraben, which serve as microbial preservatives.

Thus the facial mask broadly contemplated hereby will contain 0.5 to about 10% by weight of benzoyl peroxide thoroughly disposed throughout a blended mixture of an inorganic thickening agent, and/or an organic gelling agent, and an absorbent powder with or without alcohol. In a preferred form of this invention, excellent results are obtained with a clay based facial mask composition.

In one practice of the present invention benzoyl peroxide is blended into a master mask batch containing kaolin; a moisturizer, e.g., glycerine; SDA-40 alcohol; an inorganic thickening agent, e.g., Bentonite; and purified water USP to create a homogenous composition. The quantities of the several ingredients may vary depending on the viscosity, texture and drying properties desired in the final mix. The ranges, in percent by weight, found appropriate to create a commercially acceptable product are:

| | |
|---|---|
| Benzoyl Peroxide | 2.0–10.0 |
| Titanium Dioxide | 1.0–5.0 |
| Kaolin, USP | 20.0–25.0 |
| Glycerine (96% USP) | 2.5–15.0 |
| SDA-40 Alcohol | 0.0–10.0 |
| Bentonite | 9.0–13.0 |
| Purified water | 35.0–45.0 |

It has been found that the texture, appearance, and efficacy of the mask may be enhanced by a special manufacturing technique which produces an efficacious and cosmetically elegant product that is pleasing to use as will now be described.

In our new manufacturing process, a premix is prepared by combining a portion of the required water, Benzoyl Peroxide, Glycerin USP, Titanium Dioxide, and a portion of the Kaolin USP. These materials (in weight percent of final composition) are mixed into a slurry having the following proportions:

| | |
|---|---|
| Purified Water, USP | 22.0 |
| Benzoyl Peroxide, USP | 7.1 |
| Glycerine, USP | 12.5 |
| Kaolin, USP | 1.0 |
| Titanium Dioxide | 1.0 |

The resultant slurry is ground using conventional means and methods until it is essentialy non-gritty. Conventional grinding equipment such as ball mills, colloid mills, roller mills, homo mills, are suitable for use herein. The completeness of the grinding operation can be quantified by examining particle size under a standard microscope. A particle size of about 25μ is acceptable.

After grinding the slurry to the indicated particle size, the remainder of the ingredients are added stepwise using a conventional screw type mixer. Mixing is continued until the mixture is completely homogeneous, smooth and creamy. Thereafter the product can be readily packaged in tubes or jars for delivery to the consumer.

The preferred use of the product is accomplished once daily or as directed by the user's physician and comprises washing the affected areas thoroughly with a mild non-medicated cleanser and thereafter rinsing and pat drying the skin. Thereafter, using a circular motion, a thin layer of the mask formulation is applied evenly over the affected area and the mask is allowed to dry for 15 or 20 minutes. The face is then rinsed thoroughly with warm water to remove all of the mask and the face is dried.

As will appear, in order for benzoyl peroxide to be effective against acne, it must transit the vehicle and penetrate into the sebaceous duct through the follicular opening. Earlier studies involving commercially available vehicles indicated that benzoyl peroxide can penetrate the stratum corneum but at that level is rapidly converted into benzoic acid, an inactive form (See: *Journal of the American Academy of Dermatology*, 4, 31–37, 1981; and ibid, 9, 920–924, 1983). As will hereinafter appear, using the mask of the present invention, penetration of the active reagent into the comedone is achieved with demonstrated benefit.

To further aid in the understanding of the present invention, and not by way of limitation, the following examples are presented.

EXAMPLE I

A facial mask is prepared using the following procedure. A portion of the stated water is admixed with 0.5 to about 10% by weight (final formulation) of benzoyl peroxide, glycerine, titanium dioxide, and a portion of the absorbent powder to form a slurry. The slurry is then fine ground to a 25μ particle size. The balance of the several ingredients is then sequentially mixed into the ground slurry to produce a homogeneous smooth and creamy blend having the following compositions in percent by weight.

| | |
|---|---|
| Composition A | |
| Glycerine, 96% | 5.0% |
| Propylene Glycol | 5.0% |
| Benzoyl Peroxide | 3.4% |
| SDA-40 Alcohol | 10.0% |
| Purified Water, USP | 43.6% |
| Bentonite, USP | 11.0% |
| Kaolin, USP | 21.0% |
| Titanium Dioxide | 1.0% |
| Composition B | |
| Purified Water, USP | 42.77% |
| Kaolin, USP | 42.17% |
| Bentonite | 4.13% |
| Isopropyl Alcohol | 3.78% |
| Benzoyl Peroxide, 78% | 7.0% |
| Composition C | |
| Glycerine, 96% | 10.0% |
| Benzoyl Peroxide | 7.0% |
| SDA-40 Alcohol | 3.0% |
| Purified Water, USP | 45.9% |
| Bentonite, USP | 12.0% |
| Kaolin, USP | 21.0% |
| Titanium Dioxide | 1.0% |

EXAMPLE II

A facial mask is prepared using the following procedure. A part of the stated water is admixed with methylcellulose, benzoyl peroxide and a portion of the absorbent powder to form a slurry. The slurry is then fine ground to a 25μ particle size. The balance of the several ingredients is then sequentially mixed into the ground slurry to produce a homogeneous smooth and creamy blend having the following compositions in percent by weight.

| Composition D | |
|---|---|
| Solulan 98 | 5.0% |
| Methylcellulose (400 cps) | 1.5% |
| Benzoyl Peroxide | 5.0% |
| SDA-40 Alcohol | 5.0% |
| Purified Water, USP | 63.5% |
| Bentonite, USP | 15.0% |
| Zinc Oxide | 5.0% |
| Titanium Dioxide | 2.5% |

EXAMPLE III

A facial mask is prepared using the following procedure. A portion of the stated water is admixed with an organic gelling agent such as polyvinyl alcohol or gelatin and mixed until fully hydrated and homogeneous. A separate slurry is prepared by combining benzoyl peroxide, glycerine and Tween 20 (if used). This slurry is then fine ground to a 25μ particle size. The ground slurry and hydrated organic gellant are then combined and the remaining ingredients are sequentially mixed to produce a homogeneous smooth and creamy blend having the following compositions in percent by weight.

| Composition E | |
|---|---|
| Glycerine, 96% | 5.0% |
| Benzoyl Peroxide | 7.0% |
| SDA-40 Alcohol | 8.0% |
| Purified Water, USP | 64.0% |
| Polyvinyl Alcohol | 15.0% |
| Tween 20 | 1.0% |
| Composition F | |
| Glycerine, 96% | 3.0% |
| Gelatin | 4.0% |
| Benzoyl Peroxide | 10.0% |
| Purified Water, USP | 80.0% |
| Titanium Dioxide | 3.0% |

EXAMPLE IV

A facial mask is prepared using the following procedure. A portion of the stated water is admixed with part of the veegum, benzoyl peroxide and titanium dioxide to form a slurry. The slurry is then fine ground to a 25μ particle size. The balance of the several ingredients is then sequentially mixed into the ground slurry to produce a homogeneous smooth and creamy blend having the following compositions in percent by weight.

| Composition G | |
|---|---|
| Benzoyl Peroxide | 10.0% |
| SDA-40 Alcohol | 15.0% |
| Purified Water, USP | 62.75% |
| Veegum | 10.0% |
| Methylparaben | 0.25% |
| Titanium Dioxide | 2.0% |

EXAMPLE V

Using the procedure of Example I, clay based facial masks were prepared having the following compositions in percent by weight:

| | |
|---|---|
| Benzoyl Peroxide | 2.0–10.0 |
| Titanium Dioxide | 1.0–5.0 |
| Kaolin, USP | 20.0–25.0 |
| Glycerine (96% USP) | 2.5–15.0 |
| SDA-40 Alcohol | 0.0–10.0 |
| Bentonite | 9.0–13.0 |
| Purified water | 35.0–45.0 |

EXAMPLE VI

A clay mask according to Example V containing 5% benzoyl peroxide, USP was prepared in accordance with the procedure of Example II and applied to the right one-third forehead of twenty volunteers, from which after twenty minutes, it was washed off with warm water. The left one-third forehead of each subject was washed but without any mask application. The center third forehead of each subject was left untreated and unwashed. Each test site was then extracted for its lipid content and the quantity of lipids was gravemetrically determined and the composite results are shown in Table A below.

TABLE A

| Procedure | Quantity of sebum remaining (ug/cm$^2$) |
|---|---|
| Mask and wash | 36.01 |
| Wash only | 77.43 |
| No treatment | 208.93 |

The data clearly demonstrated the lipid adsorbing capacity of the mask in that it removed significantly ($p > 0.005$) more sebum than mere washing.

EXAMPLE VII

A clay mask preparation according to Example V containing 5% benzoyl peroxide, USP was prepared in accordance with the procedure of Example I. A panel of ten volunteers had the initial P. acnes level on each side of their face measured by the method of Williamson and Kligman (*Journal of Investigative Dermatology*, 45, 492–503, 1965) and their initial fatty acid/triglyceride ratios were determined by the method of Downing (*J. Chromatography* (38) 91–99, 1968). The clay mask prepared as indicated was applied one half of each volunteer's face once a day for twenty minutes per the specified regimen. On the other side of each volunteer face was applied Desquam-X 5% gel twice per day per label instructions. After one week, the P. acnes and free fatty acid/triglyceride levels for each subject was repeated. The cumulative reduction results in the respective levels of these accepted indicia of clinical efficacy are in Tables B and C.

TABLE B

| P. acnes reduction (log/cm$^2$) | | |
|---|---|---|
| D-X gel | Period | Mask |
| 6.24 ± 0.34 | 0 week | 6.35 ± 0.61 |
| 4.84 ± 1.09 | 1 week | 4.86 ± 0.78 |

TABLE C

| Free Fatty Acid/Triglyceride Ratio | | |
|---|---|---|
| D-X gel | Period | Mask |
| 0.29 ± 0.08 | 0 week | 0.31 ± 0.09 |
| 0.20 ± 0.04 | 1 week | 0.22 ± 0.09 |

As evidence of the effectiveness of the benzoyl peroxide, all ten subjects showed significant reduction in both P. acnes and Free Fatty Acid level. Comparing the twice daily applications of a commercial gel with the single twenty minute application of the mask, it is readily seen that the degree of reduction induced are equivalent while the mask required much less product, time and inconvenience to achieve that result.

EXAMPLE VIII

Using the non-invasive follicular biopsy technique described by Mills et al (See: *Dermatologica,* 167, 57–63, 1983) and the direct measurement of drug levels by high pressure chromotography described by Wortzman et al (See: *Journal of Investigative Dermatology,* 82, 413, 1984), a half face study was conducted to compare benzoyl peroxide penetration from the facial mask of Example IV against the penetration obtained by a standard commercially available 5% gel.

The volunteers applied the mask to one side of their face once a day and washed it off after twenty minutes. On the other side, each volunteer applied a 5% benzoyl peroxide gel twice daily without washing, per its label directions. After one week, a follicular biopsy was taken and drug levels determined. In addition, the reduction in P. acnes level was compared. The results are reported in Tables D and E.

TABLE D

| Micrograms BPO/ Comedone | | Micrograms Benzoic Acid/ Comedone | |
|---|---|---|---|
| Gel | Mask | Gel | Mask |
| 7.0 ± 2.0 | 4.8 ± 1.7 | 0.91 ± .21 | 0.95 ± .31 |

TABLE E

| Log P. acnes reduction | |
|---|---|
| Gel | Mask |
| −1.3 ± .4 | −1.0 ± .4 |

While the difference between the gel and the mask product are not statistically significant in all cases, they are significant to the baseline. Thus, the data do support the conclusion that benzoyl peroxide transits through the clay mask and penetrates into the microcomedone at a sufficient concentration to suppress P. acnes levels to the same degree as a commercially available alcoholic gel such as Desquam-X-5.

EXAMPLE IX

To determine whether benzoyl peroxide exhibits a more selective penetration when delivered in a clay mask vehicle vis-a-vis an alcoholic gel, standard Franz penetration chamber tests were conducted (See: *J. Am Acad of Dermatology,* 9, 66–73, 1983).

Using excised hairless mouse skin which is "leakier" than human skin, test materials are applied and the amount that penetrates the epidermis and the papillary dermis is measured by high performance liquid chromatography.

The results shown in Table F demonstrate that while some benzoyl peroxide products cause penetration of as much as 30–40% of their applied dose, the acne mask of the present invention shows very little cutaneous penetration. By implication, it is concluded that the mask promotes penetration almost exclusively into the follicle where the drug is effective. Thus, while the mask provides the same reductions P. acnes and free fatty acid/triglyceride ratio as the commercially available gels, it allows much less benzoyl peroxide to be absorbed systemically or to be contained intradermally.

TABLE F

| | Percutaneous Penetration of Benzoyl Peroxide | | | | | | | |
|---|---|---|---|---|---|---|---|---|
| Time | C1 | | C2 | | C3 | | Mask | |
| Hours | % | mg | % | mg | % | mg | % | mg |
| 0.5 | | | | | 1.80 | 53 | | |
| 1.0 | 3.17 | 115 | 2.67 | 259 | 2.90 | 144 | .94 | 45 |
| 2.0 | 8.77 | 320 | 7.19 | 697 | 8.31 | 413 | 1.33 | 65 |
| 3.0 | | | | | 12.8 | 637 | 1.79 | 87 |
| 4.0 | 30.6 | 1120 | 15.8 | 1538 | 14.7 | 730 | 1.88 | 91 |
| 6.0 | 39.2 | 1430 | 26.2 | 2541 | | | | |
| 23 | 41.1 | 1520 | 31.4 | 3045 | | | | |

Wherein:
C1=Clear by Design ® (2.5% BPO)
C2=Clearasil ® (5% BPO)
C3=Oxycover ® (10% BPO).

From the foregoing, it is readily apparent that improved composition and methods been herein described and illustrated which fulfill all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

What is claimed is:

1. A method of producing a facial mask effective for the treatment of acne vulgaris comprising the steps of: forming a slurry containing benzoyl peroxide, an absorbent powder and purified water; grinding said slurry until the particles thereof are 25μ or less; admixing into said slurry sequentially a thickening agent and additional solvent selected from the group consisting of purified water, and mixture of purified water and a lower alkyl alcohol to provide a homogeneous mixture; and collecting said homogeneous mixture into a container.

2. A method of producing a facial mask according to claim 1 in which said homogeneous mixture contains, in weight percent, from about 0.5 to about 10 percent benzoyl peroxide; from about 9 to about 13 percent of an inorganic thickening agent selected from the group consisting of magnesium aluminum silicate and bentonite; from about 20 to about 25 percent of kaolin; and further containing from about 2.5 to about 15 percent of a humectant selected from the group consisting of glycerine, sorbital and propylene glycol; and q.s. of a solvent selected from the group consisting of distilled water, a lower alkyl alcohol and mixtures thereof.

3. A method of producing a facial mask according to claim 2 in which said homogeneous mixture contains an organic gelling agent selected from the group consisting of gelatin, starch, cellulosic gum, guar gum, alginate and polyvinyl alcohols.

4. A method of producing a facial mask according to claim 1 in which said homogeneous mixture contains, in weight percent, from about 5 to about 10 percent benzoyl peroxide; from about 1 to about 5 percent titanium dioxide; from about 20 to about 25 percent kaolin; from about 2.5 to about 15 percent glycerine; up to about 10 percent denatured ethyl alcohol; from about 9 to about 13 percent bentonite; and q.s. distilled water.

5. A method of producing a facial mask according to claim 4 in which said homogeneous mixture contains, in weight percent, 1 percent titanium dioxide; 21 percent kaolin, 12.5 percent glycerine; 2.75 percent ethyl alcohol; 11.5 percent bentonite, and 44 percent distilled water.

* * * * *